US00PP30799P2

(12) United States Plant Patent
Beekenkamp

(10) Patent No.: US PP30,799 P2
(45) Date of Patent: Aug. 13, 2019

(54) ***BEGONIA* PLANT NAMED 'BKPBEWFEP'**

(50) Latin Name: *Begonia boliviensis*
Varietal Denomination: BKPBEWFEP

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/932,679

(22) Filed: Apr. 6, 2018

(51) Int. Cl.
*A01H 6/18* (2018.01)
*A01H 5/02* (2018.01)

(52) U.S. Cl.
USPC ..... Plt./343
CPC ..... *A01H 6/185* (2018.05)

(58) Field of Classification Search
USPC ..... Plt./343
CPC ..... A01H 6/185; A01H 6/18; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Begonia* plant named 'BKPBEWFEP', characterized by its broadly outwardly spreading to trailing plant habit; moderately freely branching habit; dark green-colored leaves; freely flowering habit; and light red-colored flowers.

2 Drawing Sheets

Botanical designation: *Begonia boliviensis.*
Cultivar denomination: 'BKPBEWFEP'.

BACKGROUND OF THE INVENTION

The present invention relates to a new and distinct cultivar of *Begonia* plant, botanically known as *Begonia boliviensis* and hereinafter referred to by the name 'BKPBEWFEP'.

The new *Begonia* plant is a product of a planned breeding program conducted by the Inventor in Maasdijk, The Netherlands. The objective of the breeding program was to develop new freely branching and freely flowering *Begonia* plants with attractive flowers and good garden performance.

The new *Begonia* plant originated from a cross-pollination made by the Inventor in September, 2014 of a proprietary selection of *Begonia boliviensis* identified as code number 6502681, not patented, as the female, or seed, parent with a proprietary selection of *Begonia boliviensis* identified as code number 6503660, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in March, 2015.

Asexual reproduction of the new *Begonia* plant by vegetative tip cuttings in a controlled greenhouse environment in Maasdijk, The Netherlands since May, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEWFEP'. These characteristics in combination distinguish 'BKPBEWFEP' as a new and distinct *Begonia* plant:

1. Broadly outwardly spreading to trailing plant habit.
2. Moderately freely branching habit.
3. Dark green-colored leaves.
4. Freely flowering habit.
5. Light red-colored flowers.

Plants of the new *Begonia* can be compared to plants of the female parent selection. Plants of the new *Begonia* differ primarily from plants of the female parent selection in the following characteristics:

1. Plants of the new *Begonia* are more freely branching than plants of the female parent selection.
2. Plants of the new *Begonia* have light red-colored flowers whereas plants of the female parent selection have orange-colored flowers.

Plants of the new *Begonia* can be compared to plants of the male parent selection. Plants of the new *Begonia* differ primarily from plants of the male parent selection in the following characteristics:

1. Plants of the new *Begonia* are more trailing than and not as upright as plants of the male parent selection.
2. Leaves of plants of the new *Begonia* are darker green than leaves of plants of the male parent selection.

Plants of the new *Begonia* can be compared to plants of the *Begonia pendula* X *Begonia boliviensis* 'BKPBEWFER', disclosed in U.S. Plant Pat. No. 24,959. In side-by-side comparisons, plants of the new *Begonia* differ from plants of 'BKPBEWFER' in the following characteristics:

1. Leaves of plants of the new *Begonia* are not as dark green in color as leaves of plants of 'BKPBEWFER'.
2. Plants of the new *Begonia* have light red-colored flowers whereas plants of 'BKPBEWFER' have bright red-colored flowers.

Plants of the new *Begonia* can be compared to plants of the *Begonia pendula* X *Begonia boliviensis* 'Encanto Orange', disclosed in U.S. Plant Pat. No. 20,898. In side-by-side comparisons, plants of the new *Begonia* differ from plants of 'Encanto Orange' in the following characteristics:

1. Plants of the new *Begonia* are more trailing than and not as upright as plants of 'Encanto Orange'.
2. Plants of the new *Begonia* have light red-colored flowers whereas plants of 'Encanto Orange' have bright orange- colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEWFEP' grown in a container.

The photograph on the second sheet are close-up views of upper and lower surfaces of typical developed and developing flowers and leaves of 'BKPBEWFEP'.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day and night temperatures ranged from 18° to 21° C. Plants were six weeks old when the photographs and the description were taken. In the following description, color references are made to The Royal Horticultural Society Colour Chart, 2015 Edition, except where general terms of ordinary dictionary significance arc used.

Botanical classification: *Begonia boliviensis* 'BKPBEWFEP'.

Parentage:

*Female, or seed, parent*.—Proprietary selection of *Begonia boliviensis* identified as code number 6502681, not patented.

*Male, or pollen, parent*.—Proprietary selection of *Begonia boliviensis* identified as code number 6503660, not patented.

Propagation:

*Type*.—By vegetative tip cuttings.

*Time to initiate roots, summer and winter*.—About one week at temperatures about 20° C. to 25° C.

*Time to produce a rooted young plant, summer*.—About 32 days at temperatures about 20° C. to 25° C.

*Time to produce a rooted young plant, winter*.—About 35 days at temperatures about 20° C. to 25° C.

*Root description*.—Fine, fibrous; typically beige in color, actual color of the roots is dependent on substrate composition, water quality, fertilizer type and formulation, substrate temperature and physiological age of roots; plants of the new *Begonia* have not been observed to form tubers.

*Rooting habit*.—Freely branching; dense.

Plant description:

*Plant and growth habit*.—Broadly outwardly spreading and eventually hanging plant habit; plant shape roughly flattened globular; moderately freely branching habit with about six basal and lateral branches developing per plant; moderately vigorous growth habit and moderate growth rate.

*Plant height, soil level to top of foliar plane*.—About 10.5 cm.

*Plant height, soil level to top of floral plane*.—About 8.8 cm.

*Plant width*.—About 26.8 cm.

*Lateral branch description*.—Length: About 9.7 cm. Diameter: About 6.5 mm. Internode length: About 1.3 cm. Strength: Moderately weak, bending with the weight of the leaves and flowers. Aspect: About 55° from the vertical and main stem axis. Texture and luster: Smooth, glabrous; glossy. Color, developing: Close to 152B. Color, fully developed: Close to 148A.

*Leaf description*.—Arrangement: Alternate, simple. Length: About 13.9 cm. Width: About 4.4 cm. Shape: Narrowly ovate to lanceolate. Apex: Acute. Base: Oblique; lobes not imbricate to imbricate. Margin: Dentate to serrate; moderately undulate. Texture and luster, upper and lower surfaces: Smooth, glabrous; slightly glossy. Venation pattern: Pinnate. Color: Developing leaves, upper surface: Close to 152A. Developing leaves, lower surface: Close to 183B. Fully expanded leaves, upper surface: Close to between 139A and N189A; venation, close to 144A. Fully expanded leaves, lower surface: Close to 183B; venation, close to 146C. Petioles: Length: About 1.3 cm. Diameter: About 3 mm. Texture and luster, upper and lower surfaces: Smooth, glabrous; moderately glossy. Strength: Low. Color, upper and lower surfaces: Close to 153A. Stipules: Quantity per leaf: Two. Length: About 3 mm. Width: About 2 mm. Shape: Ovate. Apex: Acute. Base: Broadly cuneate. Margins: Entire, ciliate. Color, upper and lower surfaces: Close to 181D; venation, close to 185A.

Flower description:

*Flowering habit*.—Rotate single male and female flowers; flowers arranged in axillary cymes; freely flowering habit with about three flowers per cyme and about 34 flowers developing per plant; flowers nodding or drooping.

*Fragrance*.—None detected.

*Natural flowering season*.—Plants begin flowering about 41 days after planting; long flowering period, plants flower freely and continuously from spring into the autumn in The Netherlands.

*Flower longevity*.—Individual flowers last about ten days on the plant; flowers not persistent.

*Inflorescence height* (*including peduncle*).—About 9.6 cm.

*Inflorescence diameter*.—About 4.7 cm.

*Flower buds*.—Length: About 2.3 cm. Diameter: About 4 mm to 12 mm. Shape: Ovate; flattened. Texture and luster: Smooth, glabrous; velvety; matte. Color: Close to 50B.

*Male flowers*.—Diameter: About 2.7 cm. Depth: About 3.7 cm. Tepals: Quantity per flower and arrangement: Four in two whorls. Length, outer tepals: About 4.4 cm. Length, inner tepals: About 3 cm. Width, outer tepals: About 2.3 cm. Width, inner tepals: About 8 mm. Shape: Narrowly ovate to ovate.

Apex: Bluntly acute. Base: Cuneate. Margin: Entire. Texture and luster, upper surface: Smooth, glabrous; velvety; matte. Texture and luster, lower surface: Smooth, glabrous; velvety; matte to slightly glossy towards the base. Color: When opening, upper surface: Close to 52B. When opening, lower surface: Close to 52A. Fully opened, upper and lower surfaces: Close to 50A; venation, close to 50A; color does not fade with development. Tepaloids: None observed on male flowers.

*Female flowers*.—Diameter: About 2.6 cm. Depth: About 3.6 cm. Tepals: Quantity per flower and arrangement: Five in two whorls. Length, outer tepals: About 3.2 cm. Length, inner tepals: About 2.8 cm. Width, outer tepals: About 1.3 cm. Width, inner tepals: About 8 mm. Shape: Narrowly ovate to ovate. Apex: Bluntly acute. Base: Cuneate. Margin: Entire. Texture and luster, upper surface: Smooth, glabrous; velvety; matte. Texture and luster, lower surface: Smooth, glabrous; velvety; matte to slightly glossy towards the base. Color: When opening, upper and lower surfaces: Close to 50A. Fully opened, upper and lower surfaces: Close to 50A; venation, close to 50A; color does not fade with development. Tepaloids: None observed on female flowers.

*Peduncles*.—Length: About 3.6 cm. Diameter: About 2 mm. Angle: About 70° from lateral branch axis. Strength: Moderately weak; flexible and bending with the weight of the flowers. Color: Close to 144A.

*Pedicels, male and female flowers*.—Length: About 2 cm. Diameter: About 1.5 mm. Angle: About 40° from the peduncle axis. Strength: Moderately weak; flexible, bending with the weight of the flowers. Texture and luster: Smooth, glabrous; glossy. Color: Close to 144B.

*Flower bracts*.—Quantity per flower and arrangement: Two, at the top of the peduncles. Length: About 1.5 cm. Width: About 1.5 cm. Shape: Roughly reniform. Apex: Abruptly acute. Base: Cordate. Margin: Ciliate. Texture and luster, upper and lower surfaces: Smooth, glabrous; matte. Color, upper and lower surfaces: Close to 179A to 179B; towards the base, close to 145C.

*Reproductive organs*.—Androecium: Present only on male flowers. Stamen quantity per flower: About 60. Filament length: About 1.5 mm. Filament color: Close to 17B. Anther size: About 1.5 mm by 1 mm. Anther shape: Broadly oblong. Anther color: Close to 4C. Amount of pollen: Scarce. Pollen color: Close to 16C. Gynoecium: Present only on female flowers. Quantity per flower: Three. Pistil length: About 8 mm. Stigma diameter: About 1.25 mm. Stigma shape: Cleft. Stigma color: Close to 15A. Style length: About 3 mm. Style color: Close to 31B. Ovary color: Close to 39B and 50A. Seeds and fruits: Seed and fruit development have not been observed on plants of the new *Begonia* to date.

Disease & pest resistance: Plants of the new *Begonia* have been observed to be resistant to *Fusarium foetens*. To date, resistance to pests and other pathogens common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEWFEP' as illustrated and described.

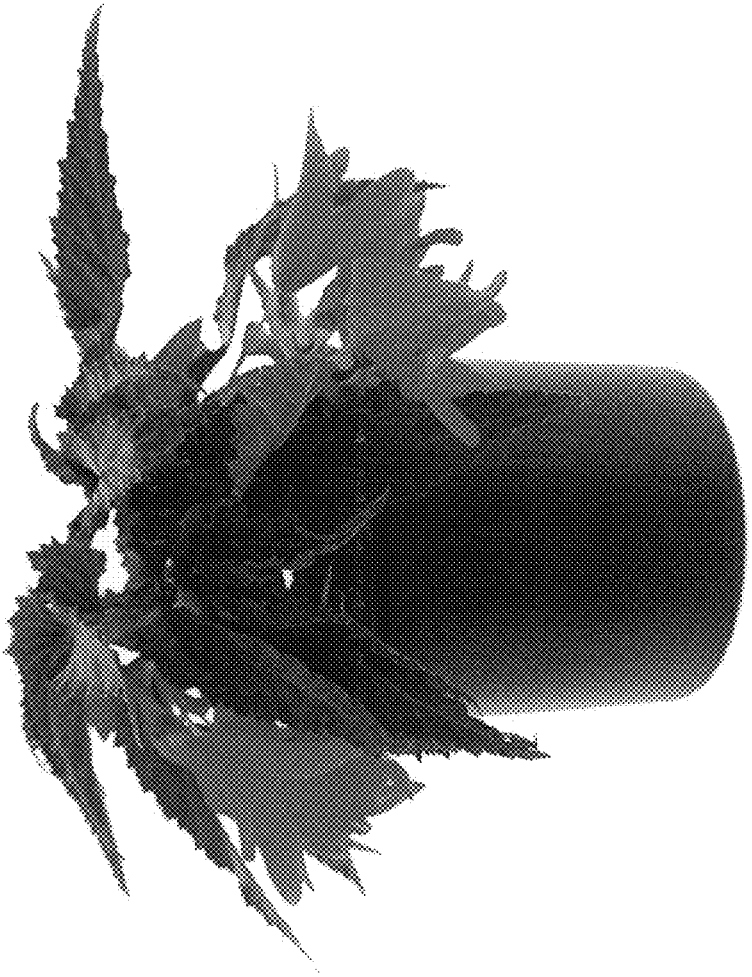

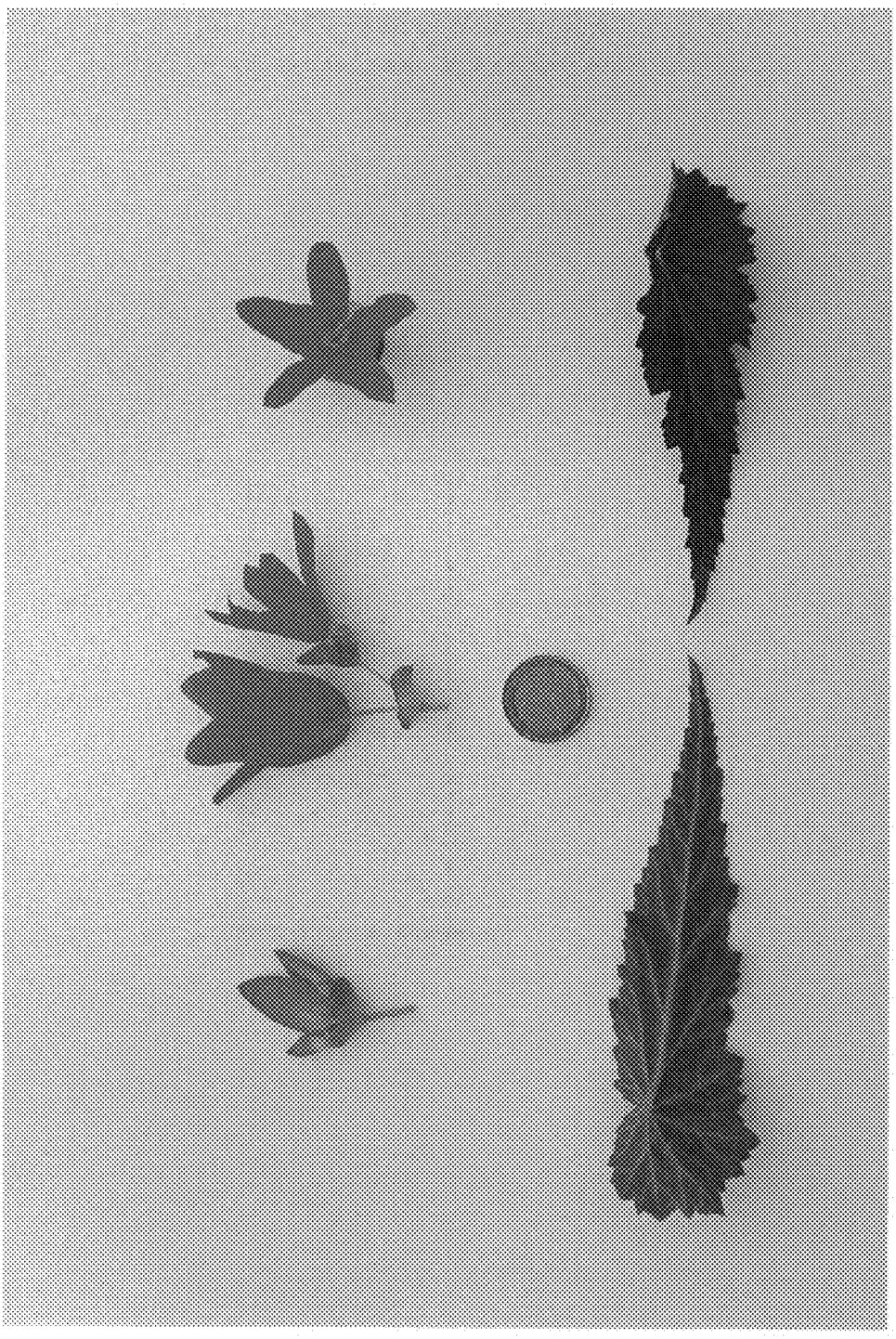

* * * * *